United States Patent [19]

Kuntz

[11] Patent Number: 4,747,166

[45] Date of Patent: May 31, 1988

[54] FLUID ASPIRATION SYSTEM FOR THE MANAGEMENT OF URINARY INCONTINENCE

[76] Inventor: David H. Kuntz, 11810 Bel Terrace, Los Angeles, Calif. 90049

[21] Appl. No.: 50,048

[22] Filed: May 15, 1987

[51] Int. Cl.$^4$ .............................................. A47K 11/00
[52] U.S. Cl. ..................................... 4/144.1; 4/144.2; 4/144.3; 4/455; 4/456; 604/329; 604/347
[58] Field of Search .............................. 4/144.1–144.4, 4/301, 114.1, 450, 452, 454, 462, 463, 455, 456; 604/347, 329, 350

[56] References Cited

U.S. PATENT DOCUMENTS

| | | | |
|---|---|---|---|
| 2,749,558 | 6/1956 | Lent et al. | 4/144.3 X |
| 2,968,046 | 1/1961 | Duke | 4/144.3 |
| 3,114,916 | 12/1963 | Hadley | 4/144.3 |
| 3,349,768 | 10/1967 | Keane | 604/347 |
| 3,757,356 | 9/1973 | Freeman | 4/456 X |
| 4,198,979 | 4/1980 | Cooney et al. | 604/329 |
| 4,360,933 | 11/1982 | Kimura | 4/144.1 X |
| 4,425,130 | 1/1984 | DesMarais | 604/358 X |

Primary Examiner—Henry K. Artis
Attorney, Agent, or Firm—Philip D. Junkins

[57] ABSTRACT

A urine aspiration system for the management of urinary incontinence comprising an absorptive pad adapted to temporarily receive and retain urine until it is drawn from the pad by an associated vacuum source. The pad comprises an absorptive core encased within a covering of hydrophobic material such as polyethylene sheet material. The upper cover sheet of the casing has a myriad of perforations to render it permeable to liquid, while the lower backing cover sheet is impermeable. Tubing from the vacuum source is coupled to a central opening of the pad so that urine may be readily drawn out of the pad when the vacuum source is activated, leaving the outer covering of the pad feeling dry and comfortable to the patient. A collection vessel is mounted between the vacuum source and the pad to collect the urine drawn from the pad.

15 Claims, 3 Drawing Sheets

FLUID ASPIRATION SYSTEM FOR THE MANAGEMENT OF URINARY INCONTINENCE

BACKGROUND OF THE INVENTION

The present invention relates to urine collection and disposal systems, and more particularly, to such systems intended for use by and for incontinent patients.

Incontinence in wheelchair and bed patients, whether in hospitals, nursing homes or at home, presents a particular and continuing problem with respect to the care of such patients. Bodily incontinence is perhaps more prevalent with the elderly. Lack of control over the urinary tract is a most frequently occurring problem and is the condition to which the present invention is directed.

In an effort to keep a bed patient's bedding clean and dry so that the patient may be made as comfortable as possible, it is frequently necessary to change the bedding several times a day for a patient lacking urinary continence. Inevitably, after a "urinary accident", there is a delay before an attendant becomes aware of the soiled and wet bedding so that steps can be taken to replace it. During this time, the patient generally cannot avoid contact with the urine-soaked bedding and suffers the discomfort, if not the development of a rash or sores, from exposure to the urine-soaked bedding. Like problems arise with respect to incontinent patients confined to wheelchairs with a continuing requirement for the changing of clothing.

There have been attempts, disclosed in the prior art, to deal with and alleviate or avoid the above-described problems associated with an incontinent bed patient. In U.S. Pat. No. 3,757,356 issued to H. Freeman there is described a therapeutic bed pan in the form of an especially configured bed pan mounted in association with a foam pad for the purpose of preventing bed sores. The foam pad rests on the top of a mattress and has a cutaway central portion in which the bed pan is mounted. The bed pan is also provided with a perforated cover and suitable connecting nozzles on opposite sides thereof. A pump to provide air and oxygen under pressure is connected to one of the nozzles while a vacuum pump is coupled to the other nozzle to remove urine from the bed pan. I. M. Timian, in U.S. Pat. No. 2,567,830 discloses a similar device (but without an associated vacuum pump) for a similar purpose.

A vacuum suction type urinating aid for male patients is disclosed in United Kingdom Patent Application GB No. 2,062,472 A. The system includes a hollow urine receptacle and a vacuum suction tube connected to a vacuum pump via a urine collector. Between the urine receptacle and the vacuum suction tube is a hollow passage containing a pair of electrodes and a wettable surface which comprise a urine detecting cylinder. When a male patient urinates into the receptacle, urine wets the wettable surface in the detecting cylinder which changes the resistance between the electrodes so that the vacuum pump is activated to draw the urine into a urine tank. The disclosure of such UK patent application is incorporated herein by reference.

A particular configuration of sanitary napkin is disclosed in U.S. Pat. No. 4,425,130 issued to T. A. DesMarais. While the sanitary napkin of the patent is particularly directed to the absorption of menstrual flow, the disclosure is of some interest for its description of the structural details and fabrication techniques for liquid absorbent pads. The disclosure of the DesMarais patent is also incorporated herein by reference.

Despite the attempts in the prior art to deal with the problems of incontinent patients outlined hereinabove, and related problems of disposing of body secretions, there remains a need for a system for use with bed and wheelchair patients (not necessarily incontinents) which can receive urine flow from a patient, whenever expelled, in an element such as an absorbent pad which can be worn by the patient without significant discomfort or inconvenience and which can have the urine drawn off from the pad to a remote receptacle which may be emptied occasionally at the convenience of the patient or an attendant. A particularly desirable feature of such a system would be a pad which is maintained so that the surface in contact with the skin of the patient always feels dry, and therefore not uncomfortable.

SUMMARY OF THE INVENTION

In brief, arrangements in accordance with the present invention comprise a system having a pump or other vacuum source, with associated urine receiving and storage receptacle, interconnected by suitable tubing to an absorptive pad which is particularly structured and configured for use in the system. A preferred embodiment of the pad incorporates a core of urine absorptive material encapsulated between an upper facing layer of liquid-permeable, hydrohobic material (such as polyethylene sheet material) and a lower, backing layer of impermeable material. The side walls of the pad are closed and may be formed by sealing the overlapping edges of the upper facing and lower backing layers, as with a suitable adhesive or by heat sealing, completely around the periphery of the core. At the proximal end of the pad there is a small opening for receiving and attaching a urine transport tube which is coupled into the vacuum system for withdrawing urine from the pad.

The core of the pad has a hollow bore extending longitudinally from the opening at its proximal end to a point within the core near the distal end of the pad. This hollow bore is generally oriented along the center of the pad and serves as a temporary receptacle for the urine which is expelled into the pad by a patient. In one embodiment of the invention, this hollow bore also is adapted to receive a perforated extension of the urine transport tube which may be inserted into the bore through the opening in the proximal end of the pad.

The core of the pad may be formed of a plurality of layers of absoptive material. In one embodiment, these layers may individually comprise highly absorbent cellulose tissue. Each layer is preferably provided with a myriad of tiny perforations extending therethrough. In an alternative embodiment, the core is formed of one or more of such perforated layers of highly absorbent cellulose tissue in the upper portion of the pad, adjacent the upper, permeable cover or facing layer, and the remainder of the core may comprise a plurality of layers of defiberized wood pulp, known in the art as "wood fluff." A single layer of cellulose tissue may be placed between the lowest layer of wood fluff and the impermeable bottom cover or backing sheet of the pad.

In an alternative arrangement, the core of the pad may comprise a sponge formed of expanded cellulose microcellular material fabricated with an open cell construction. In any event, the pad constitutes a manifold of capillary cells to which selective aspiration is applied when the pad is coupled to the urine receptacle and vacuum source of the overall system. When a pump is used, it may be connected to run continuously or it may be provided with a control box having a liquid sensor extending into the pad so that the pump is only actuated when the pad contains urine. In either case, the pump drive motor is selected to be durable, quiet, reliable and of low cost.

BRIEF DESCRIPTION OF THE DRAWING FIGURES

A better understanding of the present invention may be realized from a consideration of the following detailed descriptions, taken inconjunction with the accompanying drawing figures in which.

DETAILED DESCRIPTIONS OF THE PREFERRED EMBODIMENTS

Figure 1:
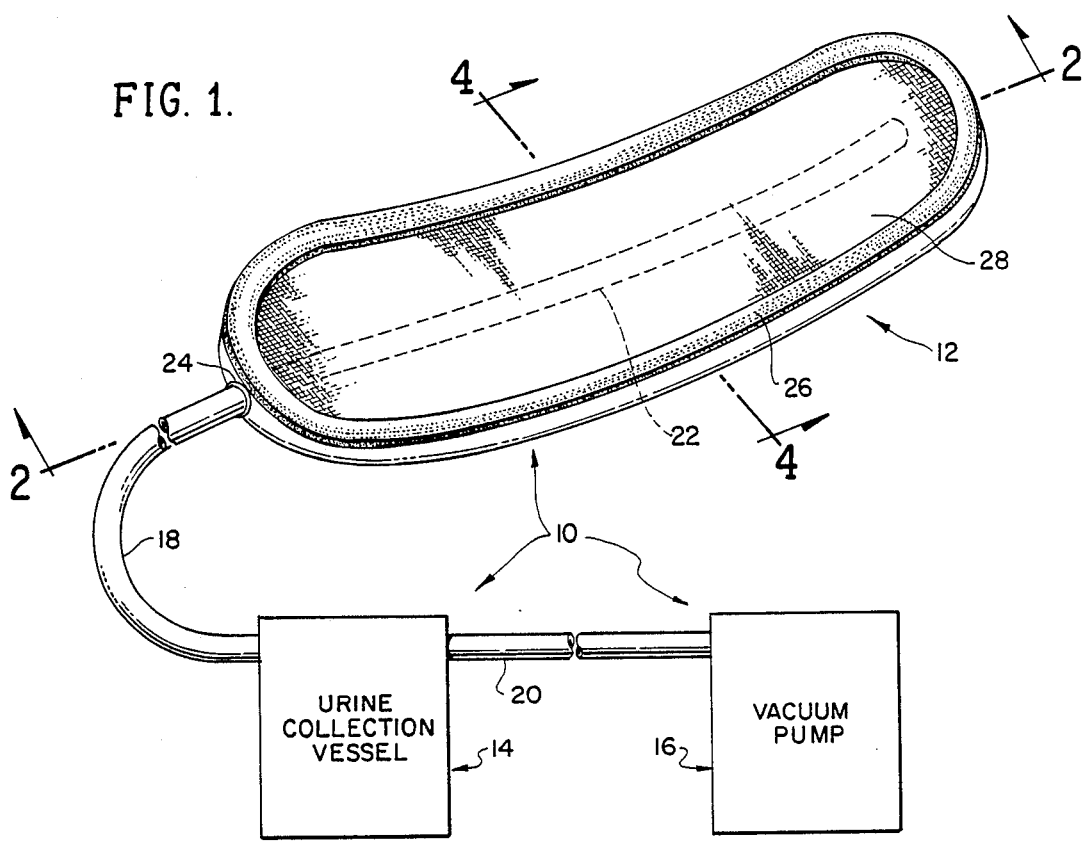
FIG. 1 is a schematic representation of the urine aspiration system for the management of urinary incontinence in accordance with the present invention.

FIG. 1 is a schematic diagram of a fluid aspiration system 10 for the management of urinary incontinence according to the invention. As shown, the system's principal components include: an absorptive pad 12, a urine collection vessel 14, and a vacuum source 16. Vacuum tubing 18 is shown coupling the pad 12 to the vessel 14. Similarly, tubing 20 extends from the urine collection vessel 14 to the vacuum source 16. The pad 12 is formed with a central bore 22 extending longitudinally of the pad along the major extent thereof from a tubing connector 24 to which tube 18 is coupled. The pad may also have a peripheral cushioning ring 26 extending about the edge of the upper facing layer 28 of the pad. The cushioning ring 26 is intended to make direct contact with the patient's body surrounding the urethral opening and facilitates the positioning of the pad to the body surface so that all urine that is expelled by the patient is passed into and absorbed by the pad. To this end, the ring 26 may be formed of a resilient foam material and, if desired, may be provided in some of its body contact areas with a skin-compatible, pressure sensitive, non-irritating adhesive on the ring surface in contact with the patient.

Figure 2:
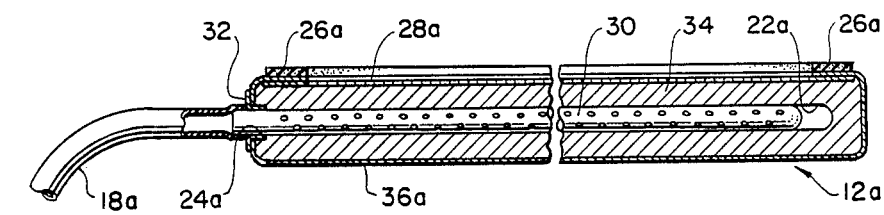
FIG. 2 is a cross-sectional view of one particular form of urine absorptive pad in accordance with the invention taken along line 2—2 of FIG. 1.
Figure 3:
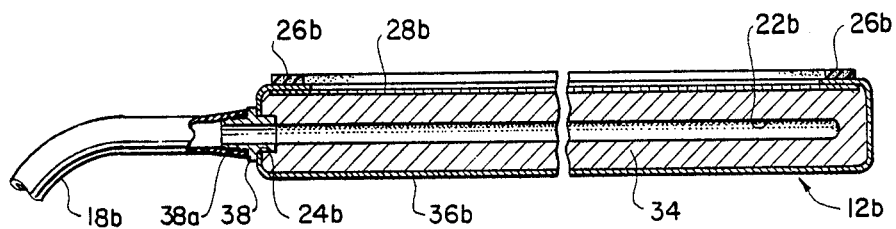
FIG. 3 is a cross-sectional view of an alternative form of urine absorptive pad taken along line 2—2 of FIG. 1.

FIGS. 2 and 3 are cross-sectional views taken along the line 2—2 of FIG. 1 and showing alternative arrangements for coupling the tube 18 to the pad 12a or 12b, respectively. In FIG. 2 the tube 18a is provided with an extended perforated end portion 30 which may be inserted within pad 12a to occupy substantially the entire extent of the hollow bore 22a of such pad. The pad 12a is shown with a retaining ring 32 extending about the opening 24 in the end of the pad. The retaining ring 32 is sufficiently flexible so that it flexes inwardly to allow the tube portion 30 to be inserted through it into the bore 22a and retains the tube portion 30 therein except against a strong outward pulling force. When the pad 12a needs to be removed from the tube 18a, the ring 32 is sufficiently resilient so that it allows the tube end portion 30 to be pulled out of the opening 24a. In this arrangement, the configuration of the pad retaining ring 32 provides a sealing effect so that air does not get by the tube to the interior of the pad 12a when the vacuum system is operating. The pad 12a is comprised of a core 34 of urine absorptive material encased by an upper facing layer 28a and a lower backing layer 36a. The lower backing layer 36a encompasses the edge portions of core 34 and is sealed to the upper facing layer 28a around the periphery of the pad 12a. A pad-to-body cushioning ring 26a surrounds the upper periphery of the pad 12a.

FIG. 3 is a similar view, taken along the same section line 2—2 of FIG. 1, of an alternative arrangement in accordance with the present invention. A pad 12b is shown with a central longitudinal bore 22b and a peripheral cushioning ring 26b. The tube 18b has a different means of connection to the pad 12b from that shown in FIG. 2, namely the end of such tube is affixed to a male connector element of coupling adaptor 38 which is sealed to the pad 12b in the area surrounding the opening 24b. The male connector element 38a of adaptor 38 is tappered and threaded so that the end of tube 18b can be forced over such element into sealing relationship therewith. In use, urine is drawn from the pad core 34 into the bore 22b and thence to the tube 18b, accomplished by suction created by the vacuum source 16 (FIG. 1).

Figure 4:
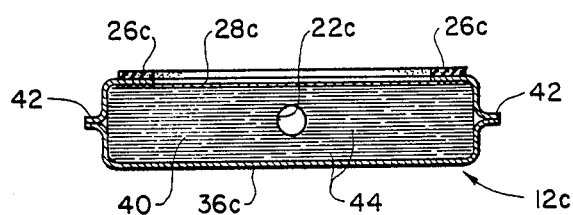
FIGS. 4, 5 and 6 are cross-sectional views taken along line 4—4 of FIG. 1 showing details of the construction of various absoptive pads which may be used in the system of FIG. 1.

FIG. 4 is a cross-sectional view of a urine receptor pad 12c taken along line 4—4 of FIG. 1 and illustrates another particular construction of the pad 12. In this embodiment, the pad 12c comprises a core 40 encased within a thin flexible outer envelope which is formed of an upper permeable layer 28c and a lower bottom covering layer 36c which is impermeable. These encasing layers 28c and 36c extend beyond the boundary of the core 40 and overlap at their peripheral edges whereat they are sealed together to form pad edge portions 42. It will be understood that the sealed edge portions extend entirely about the periphery of the pad 12c so that the core 40 is entirely enclosed, with the sole exception of an end opening (not shown) which provides access to the central bore 22c.

In FIG. 4 the core 40 as shown is made up of a plurality of thin layers 44 of highly absorbent cellulosic tissue. The bottom covering layer 36c is impermeable. The upper covering layer 28c, however, is permeable by virtue, for example, of numerous minute perforations being formed therein, as particularly shown in the detail view of FIG. 5. Both the layers 28c and 36c are preferably formed of hydrophobic material, such as polyethylene, which repels moisture. As a result, urine that has been voided onto the upper layer 28c of the pad passes through the perforations therein into the absorptive core 40 and is evacuated by the vacuum suction system which is associated therewith. The upper layer 28c of the pad feels dry and comfortable against the patient's skin within a very short time.

Figure 5:
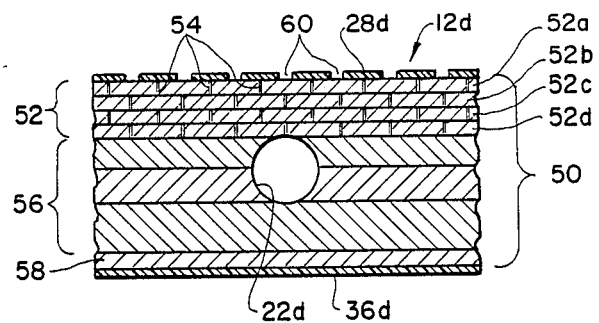

FIG. 5 is an enlarged sectional view of a portion of an alternative embodiment of the pad 12, taken along the same section line 4—4 of FIG. 1. In this arrangement, the core 50 of a pad 12d is shown having an upper section 52 comprising a plurality of layers 52a–52d of highly absorbent cellulose tissue, similar to the layers 44 of FIG. 4, except that they are provided with numerous small perforations 54 throughout their extent. The lower portion of the pad 12d, designated by the reference numeral 56, is shown comprising a plurality of layers of absorbent material in the form of convential defiberized wood pulp or so-called wood fluff. Also shown between the lowest layer of wood fluff and the bottom covering sheet 36d is a layer 58 of absorbent cellulosic tissue, like the layers 52 except that it is not perforated.

Whereas the covering layers 28d and 36d are formed of hydrophobic material so that they will dry as rapidly as possible when urine is evacuated from the core 50, the core itself is made up of highly hydrophilic material so that it will be as absorbent of liquid as possible and provide a maximum urine capacity within the given dimensions of the pad. It will be understood that the relative thicknesses and the interspersing of the stacked layers 52, 56 and 58 may be varied to control the absorbency thereof. Each layer is typically between 1/16 and ¼ inch, the cellulose tissue layers 52 being thinner than the mat layers 56. These layers may be formed as known in the prior art to establish and maintain consistency and integrity of the material making up the layers. Individual layers may be crimped, creped or embossed as appropriate to hold the constituent materials, which may be little more than loose fluff prior to processing, in place and against migration within the pad.

Covering layers 28d and 36d may typically comprise a flexible thermoplastic film, such as polyethylene, having a thickness between 0.0005 and 0.005 inches. The upper cover sheet 28d is shown with a plurality of minute openings 60 which may be present in the upper cover layer of all embodiments of the pad. These openings 60 are distributed substantially uniformly over the full area of the sheet 28d and typically have a density of between about 15 and 100 openings per square inch. As known in the art, these openings 60 may be formed by a perforating operation, such as by contacting the layer 28d with a roll covered with pins having a diameter of about 0.01 inches. Such perforating operation results in the openings 60 having a diameter of about 0.01 inches or less.

Figure 6:
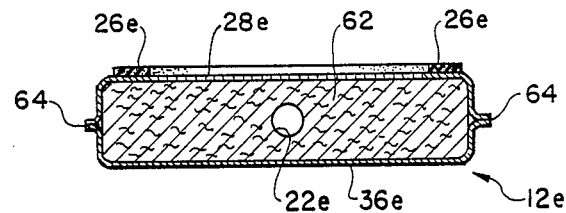

FIG. 6 is a view like that of FIG. 4 showing yet another embodiment of a pad 12e in accordance with the present invention. This pad is constructed with an outer covering layer comprising the upper cover sheet 28e and bottom layer 36e sealed together about the periphery of the core 62 at edges 64. Sheet 28e is permeable, as by perforating in the manner indicated above with respect to FIG. 5, while bottom sheet 36e is impermeable. Both sheets 28e and 36e are fabricated of hydrophobic material such as polyethylene. In the embodiment of FIG. 6 the core 62 is fabricated of expanded cellulosic microcellular material with tiny open cells throughout the core, these cells being interconnected in an open-cell sponge structure. The core 62 is thus porous and highly absorptive.

In use, any one of the absorptive pads of FIGS. 4–6, constructed in a configuration as shown in either FIG. 2 or FIG. 3, may be coupled to the tube 18 in the system of FIG. 1. The pad 12 is positioned in place on a patient to surround the urethral opening. It may be held in place by conventional means, such as adhesive, a sanitary belt, a panty garment or the like. The vacuum source or pump 16 is energized by coupling it to an electrical power source with its motor switch closed. The pump then applies a slight vacuum via the tubing 18 and 20 to the bore 22 of the pad 12. As the patient voids, urine is rapidly drawn through the perforations in the upper cover layer 28 of the pad into the porous and absorptive core where it moves by capillary action and by the effect of the pressure differential that exists between the inside and outside of the pad 12 to the central bore chamber 22. Once it reaches the bore 22, it is rapidly drawn into the tube 18 and transported to the collection vessel 14. Because of the construction of the collection vessel (one form of which is described hereinafter) and the manner in which the tubes 18 and 20 are coupled thereto, only air can be drawn into the tube 20 from the urine collection vessel 14, all urine being left in the collection vessel 14. The hydrophobic nature nature of the cover sheet 28 results in this outer sheet feeling dry and comfortable to the patient within a very short time after voiding has occurred.

Figure 7:
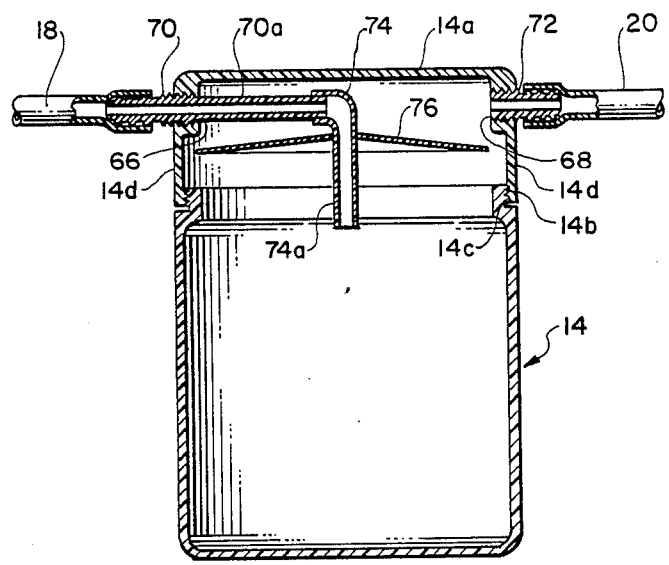
FIG. 7 is a cross-sectional view of one form of urine receiving and storage receptacle as may be used in the system of FIG. 1.

FIG. 7 shows a suitable urine collection vessel 14 with cover or cap 14a for use in the system of FIG. 1. The vessel 14 may typically be of clear glass or suitable plastic. The cap 14a is molded with a threaded coupling portion 14b to match the threads 14c on the vessel 14. The vessel cap 14a is also provided with a pair of threaded openings 66 and 68 into which tubing coupling adaptors 70 and 72, respectively, are threadably mounted. The tubing 18 and 20 may be coupled to the collection vessel 14 and cap 14a by sliding the ends of the tubing over the coupling adaptors 70 an 72 in conventional fashion. The coupling adaptor 70 has an extended pipe section 70a to which there is threaded an elbow pipe 74 which extends downwardly in pipe section 74a. The pipe section 74a bears an annular urine mist deflector 76 which extends radially across the inside of cap 14a below the threaded openings 66 and 68 of the cap, to a point in close proximity to the depending side wall 14d of the cap. Urine vapor is drawn into the collection vessel 14 through tube 18, coupling adaptor 70 and elbow pipe 74, by the vacuum source (pump) 16 acting through tube 20 and adaptor 72. Such vapor forms into droplets and collects in the lower part of the vessel. The urine collected in vessel 14 is periodically removed by unscrewing the vessel from its cap 14a and dumping same into an appropriate drain.

Figure 8:
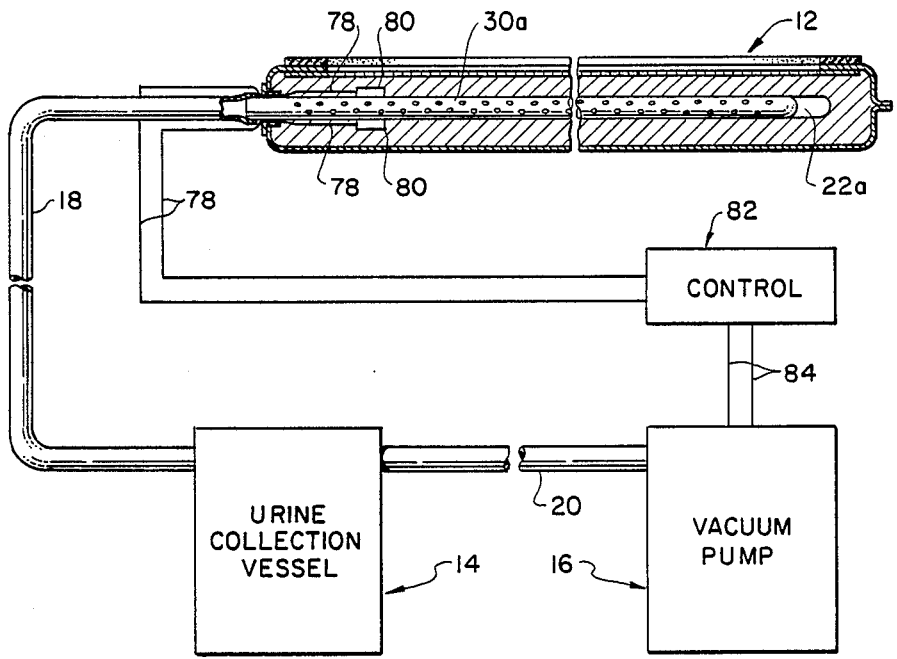
FIG. 8 is a schematic representation of an alternative urine aspiration system for the management of urinary incontinence in accordance with the invention.

An alternative arrangement of the fluid aspiration system of FIG. 1 is shown in FIG. 8 in which the added feature of a urine sensor and a control for the drive motor of the vacuum pump 16 is provided. FIG. 8 shows a pad 12 with inserted tube end portion 30a like that of FIG. 2. However, the end portion 30a is provided with a pair of leads 78 terminating in probe electrodes 80. The leads 78 extend outside of the pad 12 to a control box 82 which is coupled via electrical leads 84 to control the actuation of the motor associated with the vacuum pump 16. When the pad 12 is devoid of urine, the vacuum pump 16 is not activated. However, when urine reaches the chamber (bore) 22a, its presence is sensed by the probe electrodes 80 which provide a signal to the control box 82, causing it to activate the motor associated with the vacuum pump 16 so that the pump begins operation to draw the urine out of the pad 12.

It is to be understood that the present invention contemplates other arrangements and forms of the principal components of the fluid aspiration system for the management of urinary incontinence. For example, the vacuum or reduced pressure condition applied to the core material of the absorptive pad, to cause patient-voided urine to be drawn into the central bore of the pad's core material, may be created by various types of pumps. Thus, a roller pump may be applied directly to the tubing connected to the absorptive pad to mechanically draw urine out of the pad and actively force transfer such liquid through an extension of such tubing directly into the collection vessel. Other transfer pumps are available for withdrawing urine from the absorptive pad and passing same to the collection vessel. Also, the urine collection vessel may take many forms, both of rigid and flexible construction, and may be equiped with signal means to alert the patient and/or an attendant that the vessel is nearly full of voided urine. Finally, the absorptive pad itself may be constructed of inexpensive, short-lived natural and synthetic materials so that such pad can be treated as a disposable item to be used only for a short period of time.

By virtue of the arrangements of apparatus in accordance with the present invention which are disclosed hereinabove, an improved urine aspiration system is provided for use with incontinent patients. An absorptive pad is placed on the patient, surrounding the urethral opening, in position to receive urine which is voided by the patient. This pad includes a core which provides a manifold of capillary cells to receive and temporarily retain the urine. The application of suction to the core of the pad by an associated vacuum pump rapidly draws the urine out of this core manifold so that the patient is only temporarily discomfitted after voiding. The hydrophobic nature of the covering of the pad results in the pad feeling completely dry to the patient within a very short time.

Although there have been described above specific arrangements of a fluid aspiration system for control of urinary incontinence in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A system for the receiving and disposing of human urine excreted from an incontinent patient comprising:
   (a) an absorptive pad adapted to be placed adjacent the urinary opening of an incontinent patient, said pad having an inner core of urine-absorptive material, an upper pad facing layer of liquid-permeable hydrophobic material in contact with said patient in the area of said opening, and a lower pad backing layer of impermeable material, and said pad enclosing a flexible perforated tube extending over the length of said pad and having a fluid outlet connector means at one end thereof adjacent an edge of said pad;
   (b) a vacuum source;
   (c) a urine collection vessel; and
   (d) vacuum tubing coupling said flexible perforated tube within said pad to said collection vessel and coupling said collection vessel to said vacuum source whereby urine from said patient entering said absorptive pad through said facing layer is drawn through said absorptive pad to said perforated tube and to said collection vessel.

2. A system for the receiving and disposing of human urine excreted from an incontinent patient as claimed in claim 1 wherein the inner core of the absorptive pad comprises a plurality of layers of absorptive material positioned on opposite sides of said perforated tube.

3. A system for the receiving and disposing of human urine excreted from an incontinent patient as claimed in claim 2 wherein said layers of absorptive material are formed of highly absorbent cellulose tissue.

4. A system for the receiving and disposing of human urine excreted from an incontinent patient as claimed in claim 2 wherein said layers of absorptive material are in part formed of highly absorbent cellulose tissue and in part formed of defiberized wood pulp.

5. A system for the receiving and disposing of human urine excreted from an incontinent patient as claimed in claim 1 wherein the inner core of the absorptive pad comprises expanded cellulose microcellular material having a multiplicity of cells interconnected in open cell structure.

6. A system for the receiving and disposing of human urine excreted from an incontinent patient as claimed in claim 1 wherein said upper pad facing layer and said lower pad backing layer are formed of polyethylene sheet material and the edges of said layers are joined together to establish a seal about the periphery of said pad.

7. A system for the receiving and disposing of human urine excreted from an incontinent patient as claimed in claim 6 wherein said upper pad facing layer is perforated to establish a multiplicity of openings to facilitate the passage of urine into the inner core of urine-absorptive material.

8. A system for the receiving and disposing of human urine excreted from an incontinent patient as claimed in claim 1 wherein said absorptive pad includes a flat cushioning ring extending about the periphery of said pad on the upper pad facing layer to facilitate the positioning of said facing layer with the body of said patient.

9. A system for the receiving and disposing of human urine excreted from an incontinent patient comprising:
   (a) a flexible absorptive pad adapted to be placed adjacent the urinary opening of an incontinent patient, said pad having an inner core of urine-absorptive material with a central bore extending over a major portion of the length thereof, an upper pad facing layer of liquid-permeable hydrophobic material in contact with said patient in the area of said opening, a lower pad backing layer of impermeable material, and a fluid outlet connector means at one end of said pad adjacent an edge thereof and in fluid flow communication with said bore;
   (b) a vacuum source;
   (c) a urine collection vessel; and
   (d) vacuum tubing coupling said outlet connector means of said pad to said collection vessel and coupling said collection vessel to said vacuum source whereby urine from said patient entering said absorptive pad through said facing layer is drawn through said absorptive pad to said central bore and from said central bore through said outlet connector means and said tubing to said collection vessel.

10. A system for the receiving and disposing of human urine excreted from an incontinent patient as claimed in claim 9 wherein the outlet connector means of said pad comprises a seal between said absorptive pad and said vacuum tubing coupling said connector means to said collection vessel whereby air is precluded from entering the central bore of the inner core of urineabsorptive material of said pad.

11. A system for the receiving and disposing of human urine excreted from an incontinent patient as claimed in claim 9 wherein the vacuum tubing coupling the fluid outlet connector means of said absorptive pad to the urine collection vessel includes at its end coupled to the outlet connector means of said pad a perforated end portion adapted to extend through said connector means and into the central bore of the inner core of urine-absorptive material of said pad.

12. A system for the receiving and disposing of human urine excreted from an incontinent patient as claimed in claim 11 wherein a low voltage urine sensing means is mounted to the perforated end portion of the vacuum tubing coupled to the outlet connector means for sensing the presence of urine in the central bore of the inner core of said pad and activating the vacuum source of the system in response thereto.

13. A system for the receiving and disposing of human urine excreted from an incontinent patient as claimed in claim 9 wherein said absorptive pad includes a flat cushioning ring extending about the periphery of said pad on the upper pad facing layer to facilitate the positioning of said facing layer with the body of said patient.

14. A system for the receiving and disposing of human urine excreted from an incontinent patient as claimed in claim 9 wherein said absorptive pad includes about its periphery on the upper pad facing layer intermittent dispersions of a skin-compatible, pressure sensitive, non-irritating adhesive for contact with body areas to facilitate the positioning and maintaining of said pad in contact with the body of said patient adjacent the urinary opening of said patient.

15. A system for the receiving and disposing of human urine excreted from an incontinent patient as claimed in claim 9 wherein the flexible absorptive pad and the fluid outlet connector means at one end thereof are disposable after a limited period of use.

* * * * *